(12) United States Patent
Zheng

(10) Patent No.: US 8,585,926 B2
(45) Date of Patent: Nov. 19, 2013

(54) SUBSTITUTED BIPYRIDINES FOR USE IN LIGHT-EMITTING DEVICES

(75) Inventor: Shijun Zheng, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 13/410,602

(22) Filed: Mar. 2, 2012

(65) Prior Publication Data

US 2012/0223275 A1 Sep. 6, 2012

Related U.S. Application Data

(60) Provisional application No. 61/449,001, filed on Mar. 3, 2011.

(51) Int. Cl.
*C09K 11/06* (2006.01)

(52) U.S. Cl.
USPC .................................. 252/301.16

(58) Field of Classification Search
USPC .......................... 544/1; 252/301.16
See application file for complete search history.

(56) References Cited

U.S. PATENT DOCUMENTS

| 5,766,779 | A | 6/1998 | Shi et al. | |
|---|---|---|---|---|
| 6,541,490 | B1 | 4/2003 | Campbell et al. | |
| 6,723,445 | B2 | 4/2004 | Li et al. | |
| 7,579,353 | B2 | 8/2009 | Fiandor Roman et al. | |
| 2009/0000658 | A1* | 1/2009 | Zakeeruddin et al. | 136/252 |
| 2009/0134783 | A1 | 5/2009 | Lin et al. | |
| 2009/0214921 | A1* | 8/2009 | Uensal et al. | 429/33 |
| 2009/0306385 | A1* | 12/2009 | Walters et al. | 546/6 |

FOREIGN PATENT DOCUMENTS

| CN | 101 219 989 | 7/2008 |
|---|---|---|
| EP | 0 825 803 | 2/1998 |
| WO | WO 2009/096549 | 8/2009 |

OTHER PUBLICATIONS

Stibrany, R. T., "Exploration of Benzimidizole Chemistry," Thesis, Rutgers Univ., (2008).*
Spillane, C. B., et al., J. Inorganic Biochemistry, 102 (2008) pp. 673-683.*
Billmeyer, et al., "Principles of Color Technology", 2nd edition, John Wiley & Sons, Inc., New York, 1981.
Cheng et al., "[6,6'-Bis(benzimidazol-2-yl-N3)-2,2'-bi-pyridine]dichlorocobalt(II)-Dimethylform-amide (1/2)", Acta Crystallographica Section C, 1997, vol. C53, pp. 1238-1240.
CIE 1971, International Commission on Illumination, Colorimetry: Official Recommendations of the International Commission on Illumination, Publication CIE No. 15 (E-1.3.1) 1971, Bureau Central de la CIE, Paris, 1971.
Gustafsson et al. "Flexible Light-Emitting Diodes Made from Soluble Conducting Polymer," Nature, Jun. 11, 1992, vol. 357, pp. 477-479.

(Continued)

*Primary Examiner* — Mark Kopec
*Assistant Examiner* — William Young
(74) *Attorney, Agent, or Firm* — Knobbe Martens Olson & Bear LLP

(57) ABSTRACT

A compound represented by Formula 1 $Het^1$-Bpy-$Het^2$ is disclosed, wherein Bpy is optionally substituted 2,2'-bipyridinyl or optionally substituted 3,3'-bipyridinyl; and $Het^1$ and $Het^2$ are independently optionally substituted benzimidazol-2-yl or optionally substituted benzoxazol-2-yl. An organic light-emitting diode device comprising an organic component comprising a light-emitting component and a compound represented by Formula 1 is also disclosed.

18 Claims, 1 Drawing Sheet

| 35 |
|---|
| 30 |
| 25 |
| 15 |
| 10 |
| 5 |

(56) References Cited

OTHER PUBLICATIONS

Miao et al., "Crystal Structure of bis(3,3'-bis(1-ethyl-1H-benzimidazol-2-yl)-2,2'-bipyridine)Copper(II) Diperchlorate Monohydrate, [Cu(C28H24N6)2][ClO4]2 • H20", NCS 222, 2007, pp. 323-326.

Miao et al., "Synthesis and Crystal Structure of 3,3'-Bis(2-benzimidazolyl)-2,2'-dipyridine with Hydrated Zinc(II) Perchlorate", Chinese Journal of Structural Chemistry, 2007, vol. 26, No. 4, pp. 439-444.

Spillane et al., "Benzothiazole Bipyridine Complexes of Ruthenium(II) with Cytotoxic Activity", Journal of Biological Inorganic Chemistry, 2007, vol. 12, No. 6, pp. 797-807.

Spillane et al., "Inert Benzothiazole Functionalised Ruthenium(II) Complexes; Potential DNA Hairpin Binding Agents", Dalton Transactions, 2006, vol. 25, pp. 3122-3123.

Wang et al., "2,5. Bis [4. (9H.9. Carbazolyl) phenyl] pyridine Synthesis and Characterization", Huaxue Shiji, 2008, vol. 30, No. 4, pp. 280-282.

Yu et al., "Synthesis and Characterization of Poly(Benzobisoxazole)s and Poly(Benzobisthiazole)s with 2,2'-bipyridyl units in the Backbone", Macromolecules, 1998, vol. 31, No. 17, pp. 5639-5646.

Zhao et al., "Studies of Third-Order Optical Nonlinerities of Model Compounds Containing Benzothiazole, Benzimidazole, and Benzoxazole Units", Chemical Materials, 1990, vol. 2, pp. 670-678.

* cited by examiner

| 35 |
|----|
| 30 |
| 25 |
| 15 |
| 10 |
| 5  |

SUBSTITUTED BIPYRIDINES FOR USE IN LIGHT-EMITTING DEVICES

CROSS-REFERENCE TO RELATED APPLICATIONS

The present application claims priority under 35 U.S.C. §119(e) to U.S. Provisional Application No. 61/449,001 filed on Mar. 3, 2011, the disclosures of which is incorporated by reference herein in its entirety.

BACKGROUND OF THE INVENTION

1. Field

The embodiments relate to compounds such as substituted biaryl ring systems for use in light-emitting devices.

2. Description of the Related Art

Organic light-emitting devices (OLEDs) have been widely developed for flat panel displays, and are rapidly moving toward solid state lighting (SSL) applications. Some believe that a white OLED device with greater than 1,500 lm, a color rendering index (CRI) greater than 70, and an operating time greater than 10,000 hours at 1,000 lm/w may be useful in SSL applications. In order to reduce the driving voltage of an OLED device and extend the operational lifetime, it may be helpful to develop new high performance electron transport materials.

SUMMARY OF THE INVENTION

Some optionally substituted biaryl ring systems may be useful in electronic devices, including light-emitting devices, such as those comprising a light-emitting diode. For example, substituted bipyridine, such as optionally substituted 2,2'-bipyridinyl or optionally substituted 3,3'-bipyridinyl, may be useful in these devices. When the biaryl ring system comprises an electron withdrawing substituent on a first ring of the ring system and an electron withdrawing substituent on a second ring of the ring system, the compound may be useful in light-emitting devices or light-emitting diodes. Examples of electron withdrawing substituents may at least include, but are not limited to, a bicyclic heteroaryl comprising N, O, and/or S. For example, the biaryl ring system may comprise 1 or 2 bicyclic heteroaryl substituents, such as benzimidazol-2-yl or optionally substituted benzoxazol-2-yl. Other substituents, including electron withdrawing substituents may also be included. These compounds may be useful in electronic devices such as those comprising light-emitting diodes as host materials, electron-transport materials, electron-injecting materials, electron-injecting and electron-transport materials, hole-transport materials, and/or for materials intended for some other purpose.

Some embodiments include a compound represented by Formula 1:

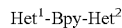

$$\text{Het}^1\text{-Bpy-Het}^2 \quad \text{(Formula 1)}$$

wherein Bpy is optionally substituted 2,2'-bipyridinyl or optionally substituted 3,3'-bipyridinyl; and Het[1] and Het[2] are independently optionally substituted benzimidazol-2-yl or optionally substituted benzoxazol-2-yl. In some embodiments, Bpy is optionally substituted 2,2'-bipyridin-6,6'-diyl or optionally substituted 3,3'-bipyridinyl.

Some embodiments include an organic light-emitting diode device comprising: an organic component comprising a light-emitting component and a compound described herein.

Some embodiments include an organic light-emitting diode device comprising: a cathode; an anode; and an organic component, disposed between the anode and the cathode, wherein the organic component comprises a light-emitting component and a compound described herein.

Some embodiments include a composition comprising a compound described herein and a fluorescent compound or a phosphorescent compound.

Some embodiments include to a composition comprising at least 10%, at least 20%, at least 50%, at least 80%, at least 90%, or at least 95%, up to about 100% by weight of a compound described herein.

These and other embodiments are described in greater detail herein.

BRIEF DESCRIPTION OF THE DRAWINGS

FIG. 1 is a schematic diagram of an embodiment of a device described herein.

DETAILED DESCRIPTION OF THE PREFERRED EMBODIMENT

Unless otherwise indicated, when a chemical structural feature such as phenyl is referred to as being "optionally substituted," it includes a feature which may have no substituents (i.e. may be unsubstituted) or which may have one or more substituents. A feature that is "substituted" has one or more substituents. The term "substituent" has the ordinary meaning known to one of ordinary skill in the art. In some embodiments, the substituent includes an ordinary organic moiety known in the art, which may have a molecular weight (e.g. the sum of the atomic masses of the atoms of the substituent) of less than: about 500 g/mol, about 300 g/mol, about 200 g/mol, about 100 g/mol, or about 50 g/mol. In some embodiments, the substituent comprises: 0-30, 0-20, 0-10, or 0-5 carbon atoms; and 0-30, 0-20, 0-10, or 0-5 heteroatoms independently selected from: N, O, S, P, Si, F, Cl, Br, I, and combinations thereof; provided that the substituent comprises at least one atom selected from: C, N, O, S, P, Si, F, Cl, Br, and I. Examples of substituents include, but are not limited to, alkyl, alkenyl, alkynyl, carbazolyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, and amino, including mono- and di-substituted amino groups, and the protected derivatives thereof. In some embodiments, the substituent may be selected from F, Cl, Br, I, $NO_2$, —CN, —CNO, —NCO, R', —OR', —COR', —$CO_2$R', —OCOR', —NR'COR", CONR'R", —NR'R", wherein each R' and R" is independently H, optionally substituted phenyl, or $C_{1-12}$ alkyl.

If a substituent comprises an optionally substituted aryl group (or "subaryl group"), such as optionally substituted phenyl, then any substituents of the subaryl group may be selected from: F, Cl, Br, I, $NO_2$, —CN, —CNO, —NCO, $R^S$, —$OR^S$, —$COR^S$, —$CO_2R^S$, —$OCOR^S$, —$NR^SCOR^{S2}$, $CONR^SR^{S2}$, —$NR^SR^{S2}$, wherein each $R^S$ and $R^{S2}$ is independently H, $C_{1-6}$ alkyl, or phenyl optionally substituted with one or more substituents independently selected from: $C_{1-3}$ alkyl, $C_{1-3}$ alkoxy, F, Cl, Br, I, or —CN.

As used herein the term "aryl" has the ordinary meaning understood by a person of ordinary skill in the art, and may include an aromatic ring or aromatic ring system such as phenyl, naphthyl, etc.

As used herein, the term "alkyl" has the ordinary meaning understood by a person of ordinary skill in the art, and may include a moiety composed of carbon and hydrogen containing no double or triple bonds. Alkyl may be linear, branched, cyclic, or a combination thereof, and in some embodiments, may contain from one to thirty-five carbon atoms. Examples of alkyl groups include but are not limited to $CH_3$ (e.g. methyl), $C_2H_5$ (e.g. ethyl), $C_3H_7$ (e.g. propyl isomers such as propyl, isopropyl, etc.), $C_3H_6$ (e.g. cyclopropyl), $C_4H_9$ (e.g. butyl isomers) $C_4H_8$ (e.g. cyclobutyl isomers such as cyclobutyl, methylcyclopropyl, etc.), $C_5H_{11}$ (e.g. pentyl isomers), $C_5H_{10}$ (e.g. cyclopentyl isomers such as cyclopentyl, methylcyclobutyl, dimethylcyclopropyl, etc.) $C_6H_{13}$ (e.g. hexyl isomers), $C_6H_{12}$ (e.g. cyclohexyl isomers), $C_7H_{15}$ (e.g. heptyl isomers), $C_7H_{14}$ (e.g. cycloheptyl isomers), $C_8H_{17}$ (e.g. octyl isomers), $C_8H_{16}$ (e.g. cyclooctyl isomers), $C_9H_{19}$ (e.g. nonyl isomers), $C_9H_{18}$ (e.g. cyclononyl isomers), $C_{10}H_{21}$ (e.g. decyl isomers), $C_{10}H_{20}$ (e.g. cyclodecyl isomers), $C_{11}H_{23}$ (e.g. undecyl isomers), $C_{11}H_{22}$ (e.g. cycloundecyl isomers), $C_{12}H_{25}$ (e.g. dodecyl isomers), $C_{12}H_{24}$ (e.g. cyclododecyl isomers), $C_{13}H_{27}$ (e.g. tridecyl isomers), $C_{13}H_{26}$ (e.g. cyclotridecyl isomers), and the like. The term "$C_{1-12}$ alkyl" as used herein, includes $C_{1-6}$ alkyl and $C_{1-3}$ alkyl.

An expression such as "$C_{1-12}$" (e.g. "$C_{1-12}$ alkyl") refers to the number of carbon atoms in a moiety, and similar expressions have similar meanings.

As used herein, the term "alkoxy" includes —O-alkyl moieties, wherein "alkyl" includes any alkyl described above.

As used herein, the term "haloalkyl" includes alkyl having one or more halo substituents (such as F, Cl, Br, or I). The term "fluoroalkyl" includes alkyl having one or more fluoro substituents. The term "$C_{1-12}$ fluoroalkyl" as used herein, includes $C_{1-6}$ fluoroalkyl and $C_{1-3}$ fluoroalkyl. The term "perfluoroalkyl" includes fluoroalkyl wherein all hydrogen atoms are replaced by fluoro such as —$CF_3$, —$C_2F_5$, —$C_3F_7$, —$C_4F_9$, etc.

The structures of some of the optionally substituted ring systems referred to herein are depicted below. These ring systems may be unsubstituted, as shown below, or a substituent may independently be in any position normally occupied by a hydrogen atom when the ring system is unsubstituted.

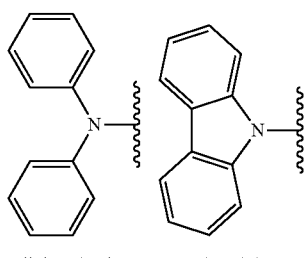

diphenylamine    carbazolyl

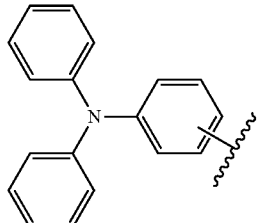

diphenylaminophenyl

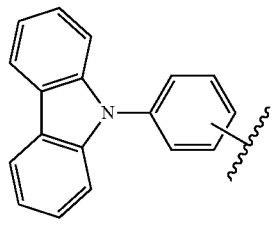

carbazolylphenyl

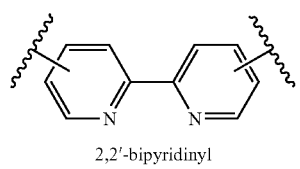

2,2'-bipyridinyl

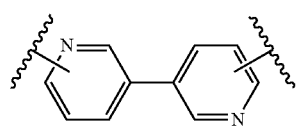

3,3'-bipyridinyl

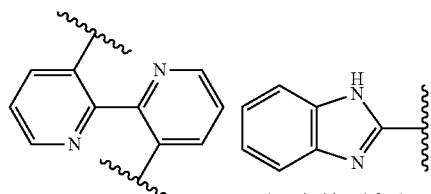

2,2'-bipyridin-6,6'-diyl    benzimidazol-2-yl

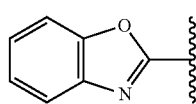

benzoxazol-2-yl

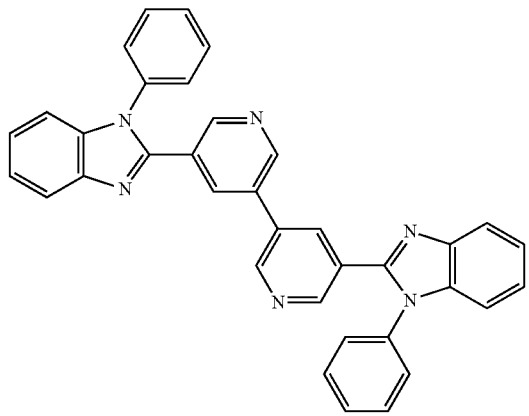

5,5'-bis(1-phenylbenzimidazol-2-yl)3,3'-bipyridine

-continued

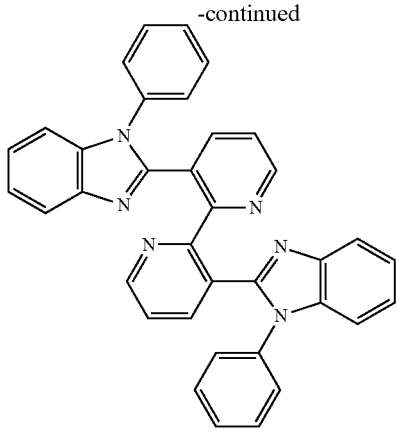

3,3'-bis(1-phenylbenzimidlazol-2-y)2,2'-bipyridine

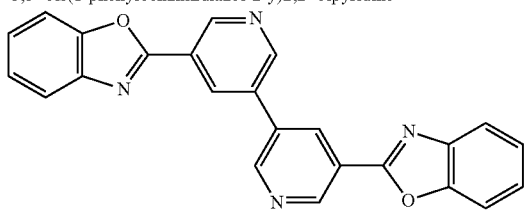

5,5'-bis(benzoxazol-2-yl)3,3'-bipyridine

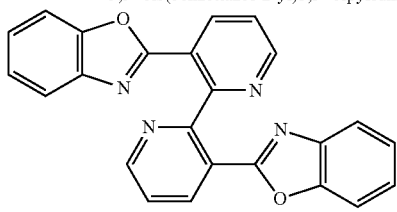

3,3'-bis(benzoxazol-2-yl)2,2'-bipyridine

The term "work function" has the ordinary meaning known to one of ordinary skill in the art. In some embodiments, a "work function" of a metal is a measure of the minimum energy required to extract an electron from the surface of the metal.

The term "high work function metal" has the ordinary meaning known to one of ordinary skill in the art, and may include a metal or alloy that easily injects holes and typically has a work function greater than or equal to about 4.5.

The term "low work function metal" has the ordinary meaning known to one of ordinary skill in the art, and may include a metal or alloy that easily loses electrons and typically has a work function less than about 4.3.

The expression "white light-emitting" has the ordinary meaning known to one of ordinary skill in the art, and may include a material is that emits white light. In some embodiments, white light may have the approximate CIE color coordinates ($X=1/3$, $Y=1/3$). The CIE color coordinates ($X=1/3$, $Y=1/3$) may be defined as the achromatic point. The X and Y color coordinates may be weights applied to the CIE primaries to match a color. A more detailed description of these terms may be found in CIE 1971, International Commission on Illumination, Colorimetry: Official Recommendations of the International Commission on Illumination, Publication CIE No. 15 (E-1.3.1) 1971, Bureau Central de la CIE, Paris, 1971 and in F. W. Billmeyer, Jr., M. Saltzman, Principles of Color Technology, 2nd edition, John Wiley & Sons, Inc., New York, 1981, both of which are hereby incorporated by reference in their entireties. The color rendering index (CRI) refers to the ability to render various colors and has values ranging from 0 to 100, with 100 being the best.

Some embodiments relate to compounds represented by at least one of Formula 2, Formula 3, Formula 4, Formula 5, Formula 6, Formula 7, Formula 8, Formula 9, Formula 10, Formula 11, Formula 12, and/or Formula 13.

Formula 2

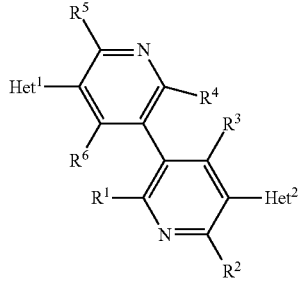

Formula 3

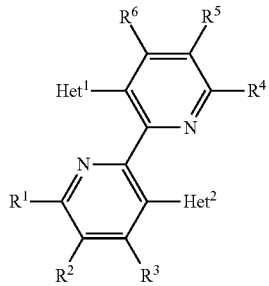

Formula 4

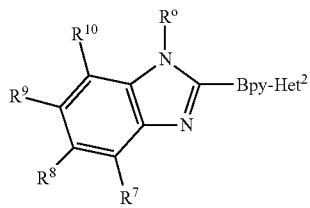

Formula 5

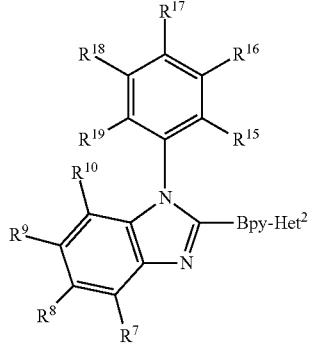

Formula 6

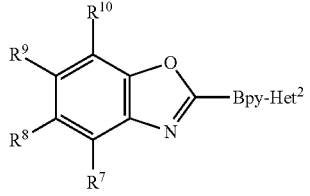

Formula 7

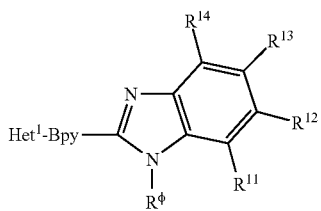

Formula 8

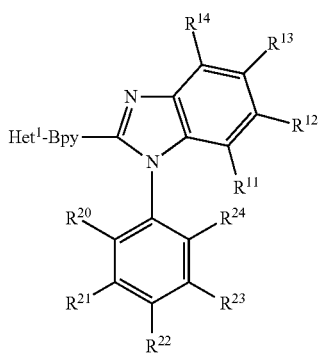

Formula 9

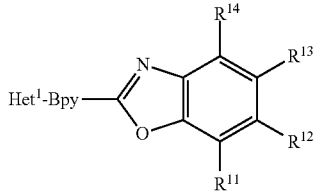

Formula 10

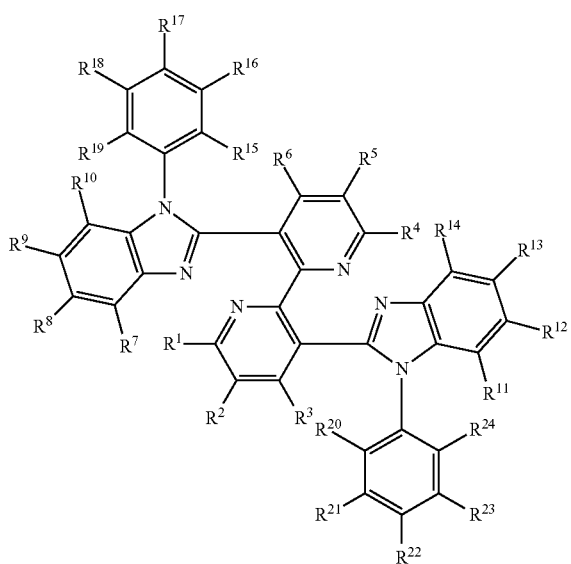

Formula 11

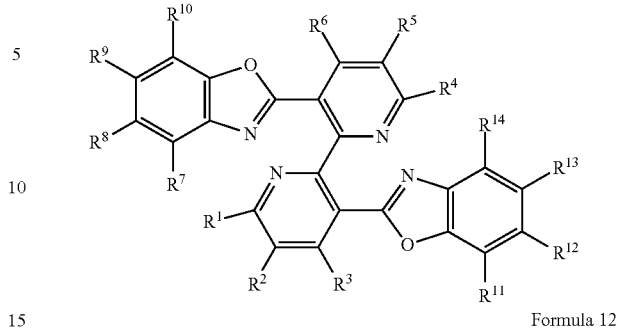

Formula 12

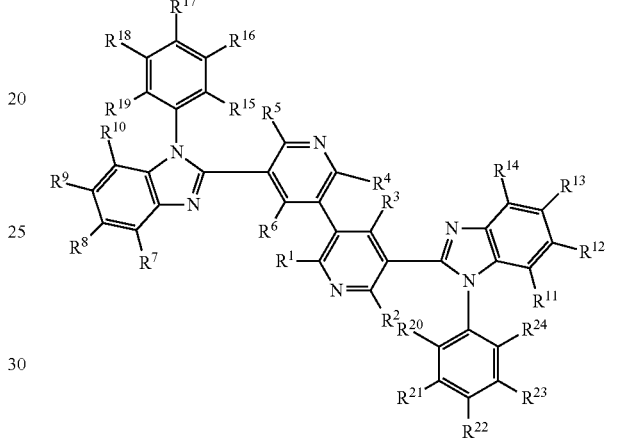

Formula 13

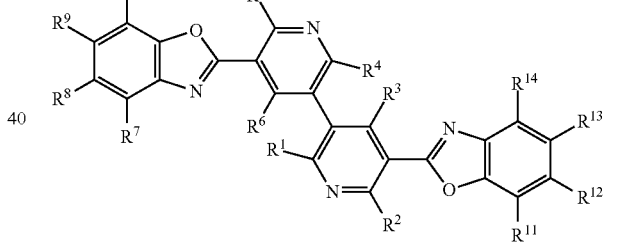

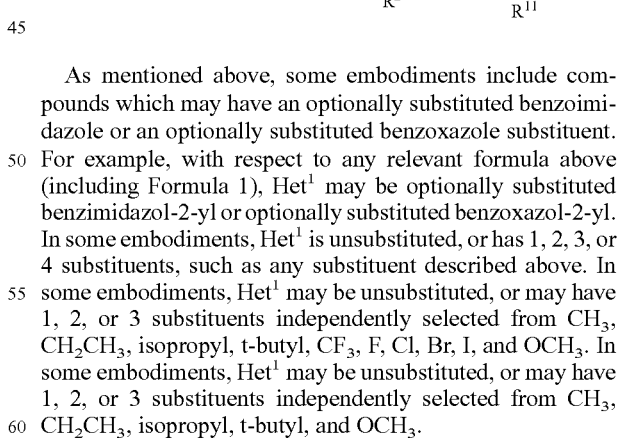

As mentioned above, some embodiments include compounds which may have an optionally substituted benzoimidazole or an optionally substituted benzoxazole substituent. For example, with respect to any relevant formula above (including Formula 1), Het¹ may be optionally substituted benzimidazol-2-yl or optionally substituted benzoxazol-2-yl. In some embodiments, Het¹ is unsubstituted, or has 1, 2, 3, or 4 substituents, such as any substituent described above. In some embodiments, Het¹ may be unsubstituted, or may have 1, 2, or 3 substituents independently selected from $CH_3$, $CH_2CH_3$, isopropyl, t-butyl, $CF_3$, F, Cl, Br, I, and $OCH_3$. In some embodiments, Het¹ may be unsubstituted, or may have 1, 2, or 3 substituents independently selected from $CH_3$, $CH_2CH_3$, isopropyl, t-butyl, and $OCH_3$.

As mentioned above, some embodiments include compounds which may have 2 or more bicyclic heteroaryl substituents, such as an optionally substituted benzoimidazole, an optionally substituted benzoxazole substituent, or both. For example, with respect to any relevant formula above, Het² may be optionally substituted benzimidazol-2-yl or optionally substituted benzoxazol-2-yl. In some embodiments, Het² is unsubstituted, or has 1, 2, 3, or 4 substituents, such as any substituent described above. In some embodiments, $Het^2$ may be unsubstituted, or may have 1, 2, or 3 substituents independently selected from $CH_3$, $CH_2CH_3$, isopropyl, t-butyl, $CF_3$, F, Cl, Br, I, and $OCH_3$. In some embodiments, $Het^2$ is unsubstituted, or has 1, 2, 3, or 4 substituents, such as any substituent described above. In some embodiments, $Het^2$ may be unsubstituted, or may have 1, 2, or 3 substituents independently selected from the group consisting of H, $C_{1-12}$ alkyl, and phenyl optionally substituted with $CH_3$, $CH_2CH_3$, isopropyl, t-butyl, or $OCH_3$.

As mentioned above, some embodiments include an optionally substituted biaryl ring systems such as optionally substituted bipyridine. For example, with respect to any relevant formula above, Bpy may be optionally substituted 2,2'-bipyridinyl, 2,2'-bipyridin-6,6'-diyl, or optionally substituted 3,3'-bipyridinyl. In some embodiments, $Het^1$ and $Het^2$ may attach to different rings of Bpy. For example, if Bpy is bipyridinyl, $Het^1$ and $Het^2$ may attach to different pyridine rings of Bpy. In some embodiments, Bpy is unsubstituted, or has 1, 2, 3, 4, 5, or 6 substituents, such as any substituent described above. In some embodiments, Bpy may be unsubstituted, or may have 1, 2, or 3 substituents independently selected from $CH_3$, $CH_2CH_3$, isopropyl, t-butyl, $CF_3$, F, Cl, Br, I, and $OCH_3$. In some embodiments, Bpy may be unsubstituted, or may have 1, 2, or 3 substituents independently selected from $CH_3$, $CH_2CH_3$, isopropyl, t-butyl, and $OCH_3$.

Any substituent may be present on any of the above described ring system, such as any substituents described herein. For example, with respect to any relevant formula above, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{24}$ may be any substituent. In some embodiments, any of $R^1$, $R^2$, $R^4$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{24}$ may independently be F, Cl, Br, I, —CN, —CNO, —NCO, R', —OR', —COR', —$CO_2R'$, —OCOR', —NR'COR", CONR'R", —NR'R", wherein each R' and R" is independently H; optionally substituted phenyl; $C_{1-12}$ alkyl such as methyl, ethyl, propyl isomers, cyclopropyl, butyl isomers, cyclobutyl isomers (such as cyclobutyl, methylcyclopropyl, etc.), pentyl isomers, cyclopentyl isomers, hexyl isomers, cyclohexyl isomers, heptyl isomers, cycloheptyl isomers, octyl isomers, cyclooctyl isomers, nonyl isomers, cyclononyl isomers, decyl isomers, cyclodecyl isomers, or the like; or $C_{1-6}$ alkyl. In some embodiments, any of $R^1$, $R^2$, $R^4$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{24}$ may independently be R', —OR', or —NR'R".

In some embodiments related to Formula 2, at least one 1, at least 3, or all of: $R^1$, $R^2$, $R^3$, $R^4$, $R^5$, and $R^6$, may be independently selected from the group consisting of H, F, Cl, Br, I, —CN, $C_{1-12}$ alkyl, $C_{1-12}$ fluoroalkyl, and optionally substituted phenyl. In some embodiments, at least one 1, at least 3, or all of: $R^1$, $R^2$, $R^3$, $R^4$, $R^5$, and $R^6$, may be independently selected from the group consisting of H, $C_{1-12}$ alkyl, and optionally substituted phenyl.

In some embodiments related to Formula 3, at least one 1, at least 3, or all of: $R^1$, $R^2$, $R^3$, $R^4$, $R^5$, and $R^6$, may be independently selected from the group consisting of H, F, Cl, Br, I, —CN, $C_{1-12}$ alkyl, $C_{1-12}$ fluoroalkyl, and optionally substituted phenyl. In some embodiments, at least one 1, at least 3, or all of: $R^1$, $R^2$, $R^3$, $R^4$, $R^5$, and $R^6$, may be independently selected from the group consisting of H, $C_{1-12}$ alkyl, and optionally substituted phenyl.

With respect to Formula 4, $R^o$ may be optionally substituted aryl. In some embodiments, at least one 1, at least 2, or all of: $R^7$, $R^8$, $R^9$, and $R^{10}$, may be independently selected from the group consisting of H, F, Cl, Br, I, —CN, $C_{1-12}$ alkyl, $C_{1-12}$ fluoroalkyl, and optionally substituted phenyl. In some embodiments, at least one 1, at least 2, or all of: $R^7$, $R^8$, $R^9$, and $R^{10}$, may be independently selected from the group consisting of H, $C_{1-12}$ alkyl, and optionally substituted phenyl.

In some embodiments related to Formula 5, at least one 1, at least 3, at least 6, or all of: $R^7$, $R^8$, $R^9$, $R^{10}$, $R^{15}$, $R^{16}$, $R^{17}$, $R^{18}$, and $R^{19}$, may be independently selected from the group consisting of H, F, Cl, Br, I, —CN, $C_{1-12}$ alkyl, $C_{1-12}$ fluoroalkyl, and optionally substituted phenyl. In some embodiments, at least one 1, at least 3, at least 6, or all of: $R^7$, $R^8$, $R^9$, $R^{10}$, $R^{15}$, $R^{16}$, $R^{17}$, $R^{18}$, and $R^{19}$, may be independently selected from the group consisting of H, $C_{1-12}$ alkyl, and optionally substituted phenyl.

In some embodiments related to Formula 6, at least one 1, at least 2, or all of: $R^7$, $R^8$, $R^9$, and $R^{10}$, may be independently selected from the group consisting of H, F, Cl, Br, I, —CN, $C_{1-12}$ alkyl, $C_{1-12}$ fluoroalkyl, and optionally substituted phenyl. In some embodiments, at least one 1, at least 2, or all of: $R^7$, $R^8$, $R^9$, and $R^{10}$, may be independently selected from the group consisting of H, $C_{1-12}$ alkyl, and optionally substituted phenyl.

With respect to Formula 7, $R^\Phi$ may be optionally substituted aryl. In some embodiments, at least one 1, at least 2, or all of: $R^{11}$, $R^{12}$, $R^{13}$, and $R^{14}$, may be independently selected from the group consisting of H, F, Cl, Br, I, —CN, $C_{1-12}$ alkyl, $C_{1-12}$ fluoroalkyl, and optionally substituted phenyl. In some embodiments, at least one 1, at least 2, or all of: $R^{11}$, $R^{12}$, $R^{13}$, and $R^{14}$, may be independently selected from the group consisting of H, $C_{1-12}$ alkyl, and optionally substituted phenyl.

In some embodiments related to Formula 8, at least one 1, at least 3, at least 6, or all of: $R^{11}$, $R^{12}$, $R^{13}$, $R^{14}$, $R^{20}$, $R^{21}$, $R^{22}$, $R^{23}$, and $R^{24}$, may be independently selected from the group consisting of H, $C_{1-12}$ alkyl, and optionally substituted phenyl. In some embodiments, at least one 1, at least 3, at least 6, or all of: $R^{11}$, $R^{12}$, $R^{13}$, $R^{14}$, $R^{20}$, $R^{21}$, $R^{22}$, $R^{23}$, and $R^{24}$, may be independently selected from the group consisting of H, $C_{1-12}$ alkyl, and optionally substituted phenyl.

In some embodiments related to Formula 9, at least one 1, at least 2, or all of: $R^{11}$, $R^{12}$, $R^{13}$, and $R^{14}$, may be independently selected from the group consisting of H, F, Cl, Br, I, —CN, $C_{1-12}$ alkyl, $C_{1-12}$ fluoroalkyl, and optionally substituted phenyl. In some embodiments, at least one 1, at least 2, or all of: $R^{11}$, $R^{12}$, $R^{13}$, and $R^{14}$, may be independently selected from the group consisting of H, $C_{1-12}$ alkyl, and optionally substituted phenyl.

In some embodiments related to Formula 10, at least 1, at least 5, at least 10, at least 15, at least 20, or all of: $R^1$, $R^2$, $R^4$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{24}$, may be independently selected from the group consisting of H, F, Cl, Br, I, —CN, $C_{1-12}$ alkyl, $C_{1-12}$ fluoroalkyl, and optionally substituted phenyl. In some embodiments, at least 1, at least 5, at least 10, at least 15, at least 20, or all of: $R^1$, $R^2$, $R^4$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{24}$, may be independently selected from the group consisting of H, $C_{1-12}$ alkyl, and optionally substituted phenyl.

In some embodiments related to Formula 11, at least 1, at least 5, at least 10, or all of: $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$, may be independently selected from the group consisting of H, F, Cl, Br, I, —CN, $C_{1-12}$ alkyl, $C_{1-12}$ fluoroalkyl, and optionally substituted phenyl. In some embodiments at least 1, at least 5, at least 10, or all of: $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$, may be independently selected from the group consisting of H, $C_{1-12}$ alkyl, and optionally substituted phenyl.

In some embodiments related to Formula 12, at least 1, at least 5, at least 10, at least 15, at least 20, or all of: $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}$ and $R^{24}$, may be independently selected from the group consisting of H, F, Cl, Br, I, —CN, $C_{1-12}$ alkyl, $C_{1-12}$ fluoroalkyl, and optionally substituted phenyl. In some embodiments, at least 1, at least 5, at least 10, at least 15, at least 20, or all of: $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}$ and $R^{24}$, may be independently selected from the group consisting of H, $C_{1-12}$ alkyl, and optionally substituted phenyl.

In some embodiments related to Formula 13, at least 1, at least 5, at least 10, or all of: $R^1, R^2, R^3, R^4, R^5, R^6, R^7, R^8, R^9, R^{10}, R^{11}, R^{12}, R^{13}$, and $R^{14}$, may be independently selected from the group consisting of H, F, Cl, Br, I, —CN, $C_{1-12}$ alkyl, $C_{1-12}$ fluoroalkyl, and optionally substituted phenyl. In some embodiments, at least 1, at least 5, at least 10, or all of: $R^1, R^2, R^3, R^4, R^5, R^6, R^7, R^8, R^9, R^{10}, R^{11}, R^{12}, R^{13}$, and $R^{14}$, may be independently selected from the group consisting of H, $C_{1-12}$ alkyl, and optionally substituted phenyl.

Some embodiments provide optionally substituted 5,5'-bis(1-phenylbenzimidazol-2-yl)3,3'-bipyridine, optionally substituted 3,3'-bis(1-phenylbenzimidlazol-2-y)2,2'-bipyridine, optionally substituted 5,5'-bis(benzoxazol-2-yl)3,3'-bipyridine, or optionally substituted 3,3'-bis(benzoxazol-2-yl)2,2'-bipyridine.

The compounds and compositions described herein can be incorporated into light-emitting devices in various ways. For example, an embodiment provides an organic component disposed between an anode and a cathode. In some embodiments, the device is configured so that holes can be transferred from the anode to the organic component. In some embodiments, the device is configured so that electrons can be transferred from the cathode to the organic component. The organic component may comprise the compounds and/or compositions described herein.

An anode layer may comprise a conventional material such as a metal, mixed metal, alloy, metal oxide or mixed-metal oxide, or a conductive polymer. Examples of suitable metals include the metals in Groups 10, Group 11, and Group 12 transition metals. If the anode layer is to be light-transmitting, mixed-metal oxides of Groups 12, Group 13, and Group 14 metals or alloys thereof, such as zinc oxide, tin oxide, indium zinc oxide (IZO) or indium-tin-oxide (ITO) may be used. The anode layer may include an organic material such as polyaniline, e.g., as described in "Flexible light-emitting diodes made from soluble conducting polymer," Nature, vol. 357, pp. 477-479 (11 Jun. 1992). Examples of suitable high work function metals include but are not limited to Au, Pt, indium-tin-oxide (ITO), or alloys thereof. In some embodiments, the anode layer can have a thickness in the range of about 1 nm to about 1000 nm.

A cathode layer may include a material having a lower work function than the anode layer. Examples of suitable materials for the cathode layer include those selected from alkali metals of Group 1, Group 2 metals, Group 11, Group 12, and Group 13 metals including rare earth elements, lanthanides and actinides, materials such as aluminum, indium, calcium, barium, samarium and magnesium, and combinations thereof. Li-containing organometallic compounds, LiF, and Li2O may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

In some embodiments, the organic component may comprise at least one light-emitting layer comprising a light-emitting component, and optionally, a host, such as a compound described herein, a hole-transport material, an electron-transport material, or an ambipolar material. In some embodiments, the device is configured so that holes can be transferred from the anode to the light-emitting layer. In some embodiments, the device is configured so that electrons can be transferred from the cathode to the light-emitting layer. If present, the amount of the host in a light-emitting layer can vary. In one embodiment, the amount of a host in a light-emitting layer is in the range of from about 1% to about 99.9% by weight of the light-emitting layer. In another embodiment, the amount of a host in a light-emitting layer is in the range of from about 90% to about 99% by weight of the light-emitting layer. In another embodiment, the amount of a host in a light-emitting layer is about 97% by weight of the light-emitting layer.

In some embodiments, the mass of the light-emitting component is about 0.1% to about 10%, about 1% to about 5%, or about 3% of the mass of the light-emitting layer. In some embodiments, the light-emitting layer may be a neat light-emitting layer, meaning that the light-emitting component is about 100% by weight of the light-emitting layer, or alternatively, the light-emitting layer consists essentially of light-emitting component. The light-emitting component may be a fluorescent and/or a phosphorescent compound. In some embodiments, the light-emitting component comprises a phosphorescent material.

The light-emitting component or compound may be chosen to vary the color of the light emitted by the light-emitting device. For example, a blue light-emitting component may emit a combination of visible photons so that the light appears to have a blue quality to an observer. In some embodiments, a blue light-emitting component may emit visible photons having an average wavelength in the range of about 440 nm or about 460 nm to about 490 nm or about 500 nm. The "average wavelength" of visible photons may include, when referring to the visible emission spectrum of a compound, the wavelength wherein the area under the curve for the part of the visible spectrum having a lower wavelength than the average wavelength is about equal to the area under the curve for the part of the visible spectrum having a higher wavelength than the average wavelength. Some non-limiting examples of compounds which may form part or all of a blue light-emitting component include iridium coordination compounds such as: bis-{2-[3,5-bis(trifluoromethyl)phenyl]pyridinato-N,C2'}iridium(III)-picolinate, bis(2-[4,6-difluorophenyl]pyridinato-N,C2')iridium (III) picolinate, bis(2-[4,6-difluorophenyl]pyridinato-N,C2')iridium(acetylacetonate), Iridium (III) bis(4,6-difluorophenylpyridinato)-3-(trifluoromethyl)-5-(pyridine-2-yl)-1,2,4-triazolate, Iridium(III)bis(4,6-difluorophenylpyridinato)-5-(pyridine-2-yl)-1H-tetrazolate, bis[2-(4,6-difluorophenyl)pyridinato-N, $C^{2'}$]iridium(III)tetra(1-pyrazolyl)borate, etc.

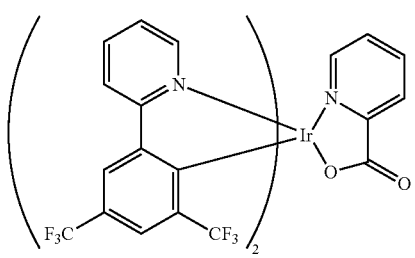

bis-{2-[3,5-bis(trifluoromethyl)phenyl]pyridinato-N,C2'}iridium(III)-picolinate(Ir(CF3ppy)2(Pic)

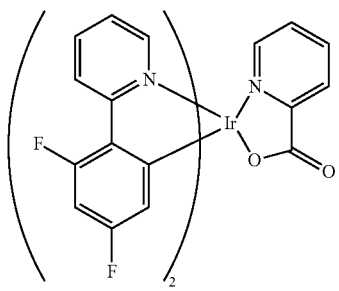

bis-(2-[4,6-difluorophenyl]pyridinato-N,C2')iridium(III)-picolinate [FIrPic]

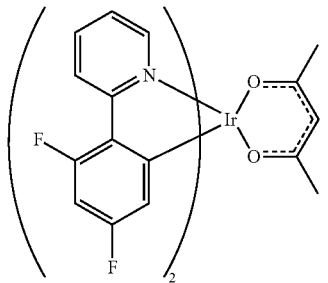

bis-(2-[4,6-difluorophenyl]pyridinato-N,C2')iridium(acetylacetonate [FIr(acac)]

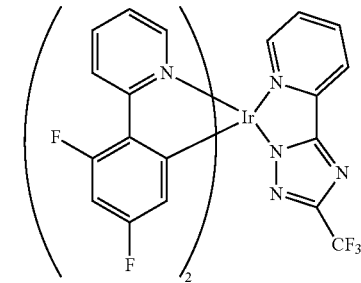

Iridium (III) bis(4,6-difluorophenylpyridinato)-3-(trifluoromethyl)-5-(pyridine-2-yl)-1,2,4-triazolate (FIrtaz)

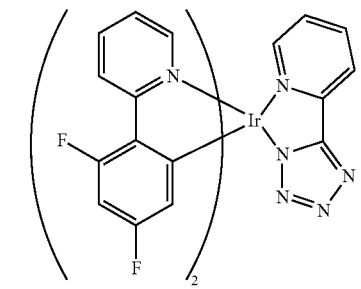

Iridium (III) bis(4,6-difluorophenylpyridinato)-5-(pyridine-2-yl)-1H-tetrazolate (FIrN4)

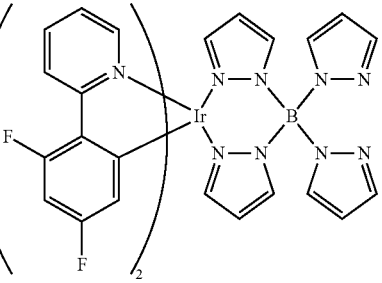

bis[2-(4,6-difluorphenyl)pyridinato-N,C2']iridium(III)tetra(1-pyrazolyl)borate (Fir6)

A red light-emitting component may emit a combination of visible photons so that the light appears to have a red quality to an observer. In some embodiments, a red light-emitting component may emit visible photons having an average wavelength in the range of about 600 nm or about 620 nm to about 780 nm or about 800 nm. Some non-limiting examples of compounds which may form part or all of a red light-emitting component include iridium coordination compounds such as: Bis[2-(2'-benzothienyl)-pyridinato-N,C3']iridium (III)(acetylacetonate); Bis[(2-phenylquinolyl)-N,C2']iridium (III) (acetylacetonate); Bis[(1-phenylisoquinolinato-N,C2')]iridium (III) (acetylacetonate); Bis[(dibenzo[f, h]quinoxalino-N,C2')iridium (III)(acetylacetonate); Tris(2,5-bis-2'-(9',9'-dihexylfluorene)pyridine)iridium (III); Tris[1-phenylisoquinolinato-N,C2']iridium (III); Tris-[2-(2'-benzothienyl)-pyridinato-N,C3']iridium (III); Tris[1-thiophen-2-ylisoquinolinato-N,C3']iridium (III); and Tris[1-(9,9-dimethyl-9H-fluoren-2-yl)isoquinolinato-(N,C3')iridium (III)), etc.

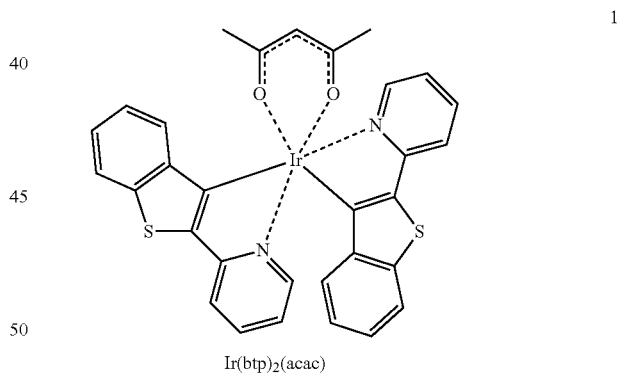

Ir(btp)2(acac)

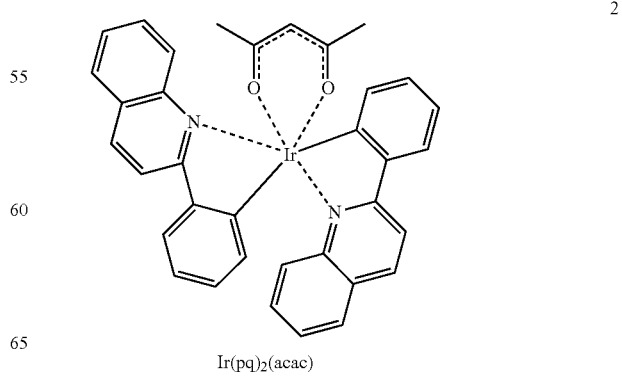

Ir(pq)2(acac)

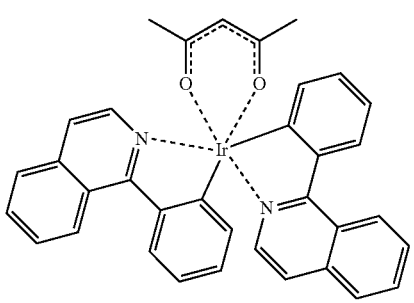

Ir(piq)₂(acac)

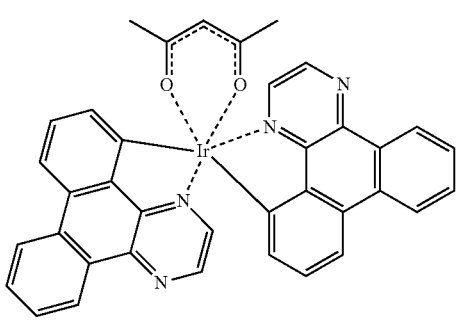

Ir(DBQ)₂(acac)

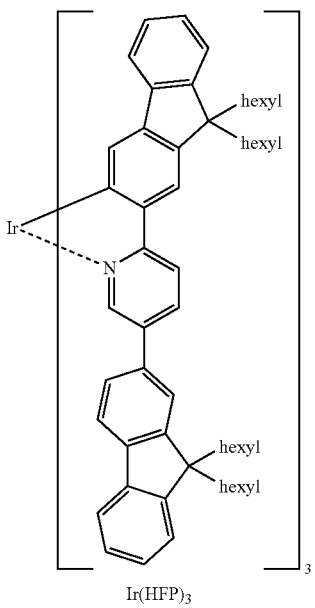

Ir(HFP)₃

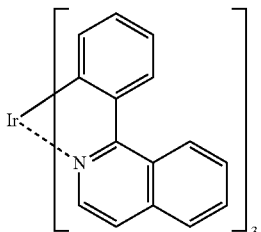

Ir(piq)₃

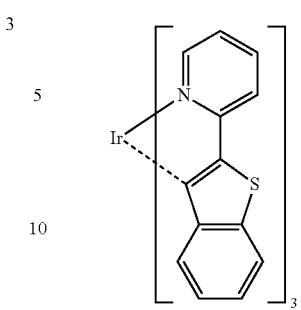

Ir(btp)₃

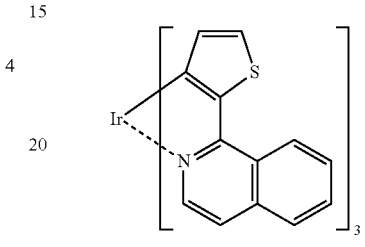

Ir(tiq)₃

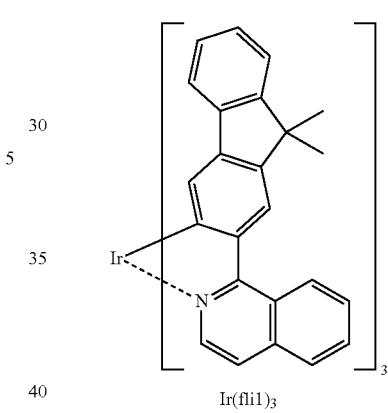

Ir(fli1)₃

1. (Btp)₂Ir(III)(acac); Bis[2-(2'-benzothienyl)-pyridinato-N,C3']iridium (III)(acetylacetonate)
2. (Pq)₂Ir(III)(acac); Bis[(2-phenylquinolyl)-N,C2']iridium (III) (acetylacetonate)
3. (Piq)₂Ir(III)(acac); Bis[(1-phenylisoquinolinato-N,C2')]iridium (III) (acetylacetonate)
4. (DBQ)₂Ir(acac); Bis[(dibenzo[f,h]quinoxalino-N,C2')iridium (III)(acetylacetonate)
5. [Ir(HFP)₃], Tris(2,5-bis-2'-(9',9'-dihexylfluorene)pyridine)iridium (III)
6. Ir(piq)₃, Tris[1-phenylisoquinolinato-N,C2']iridium (III)
7. Ir(btp)₃, Tris-[2-(2'-benzothienyl)-pyridinato-N,C3']iridium (III)
8. Ir(tiq)₃, Tris[1-thiophen-2-ylisoquinolinato-N,C3']iridium (III)
9. Ir(fliq)₃; Tris[1-(9,9-dimethyl-9H-fluoren-2-yl)isoquinolinato-(N,C3')iridium (III))

A green light-emitting component may emit a combination of visible photons so that the light appears to have a green quality to an observer. In some embodiments, a green light-emitting component may emit visible photons having an average wavelength in the range of about 490 nm or about 500 nm to about 570 nm or about 600 nm. Some non-limiting examples of compounds which may form part or all of a green light-emitting component include iridium coordination compounds such as: Bis(2-phenylpyridinato-N,C2')iridium(III) (acetylacetonate) [Ir(ppy)₂(acac)], Bis(2-(4-tolyl)pyridinato-N,C2')iridium(III)(acetylacetonate) [Ir(mppy)₂(acac)], Bis (2-(4-tert-butyl)pyridinato-N,C2')iridium (III) (acetylacetonate) [Ir(t-Buppy)₂(acac)], Tris(2-phenylpyridinato-N,C2')iridium (III) [Ir(ppy)₃], Bis(2-phenyloxazolinato-N,C2')iridium (III) (acetylacetonate) [Ir(op)₂(acac)], Tris(2-(4-tolyl)pyridinato-N,C2')iridium(III) [Ir(mppy)₃], etc.

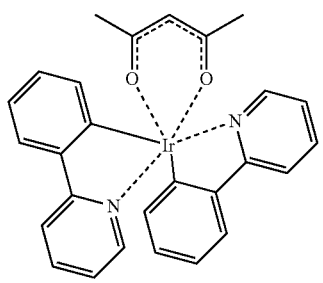

Ir(ppy)₂(acac)

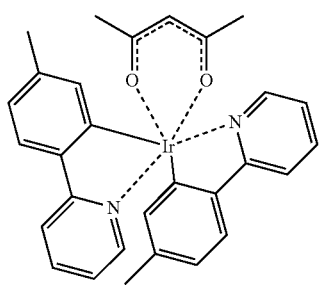

Ir(mppy)₂(acac)

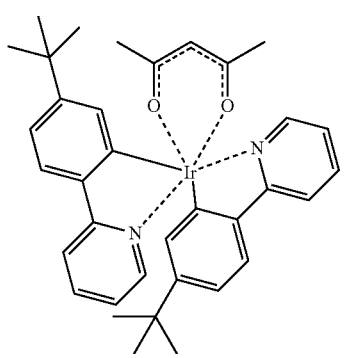

Ir(t-Buppy)₂(acac)

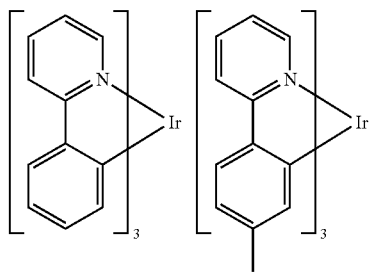

Ir(ppy)₃    Ir(mppy)₃

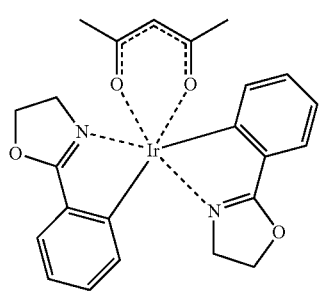

Ir(op)₂(acac)

An orange light-emitting component may emit a combination of visible photons so that the light appears to have an orange quality to an observer. In some embodiments, an orange light-emitting component may emit visible photons having an average wavelength in the range of about 570 nm or about 585 nm to about 620 nm or about 650 nm. Some non-limiting examples of compounds which may form part or all of an orange light-emitting component include iridium coordination compounds such as: Bis[2-phenylbenzothiazolato-N,C2']iridium (III)(acetylacetonate), Bis[2-(4-tert-butylphenyl)benzothiazolato-N,C2']iridium(III)(acetylacetonate), Bis[(2-(2'-thienyl)pyridinato-N,C3')]iridium (III) (acetylacetonate), Tris[2-(9,9-dimethylfluoren-2-yl)pyridinato-(N,C3')]iridium (III), Tris[2-(9,9-dimethylfluoren-2-yl)pyridinato-(N,C3')]iridium (III), Bis[5-trifluoromethyl-2-[3-(N-phenylcarbzolyl)pyridinato-N,C2']iridium(III) (acetylacetonate), (2-PhPyCz)₂Ir(III)(acac), etc.

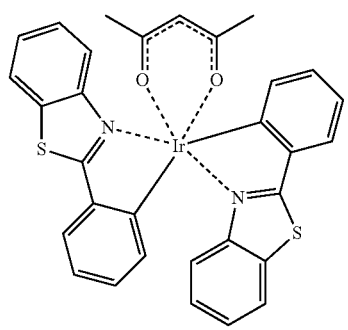

(bt)₂Ir(III)(acac)
Bis[2-phenylbenzothiazolato-N,C2'] iridium (III)(acetylacetonate)

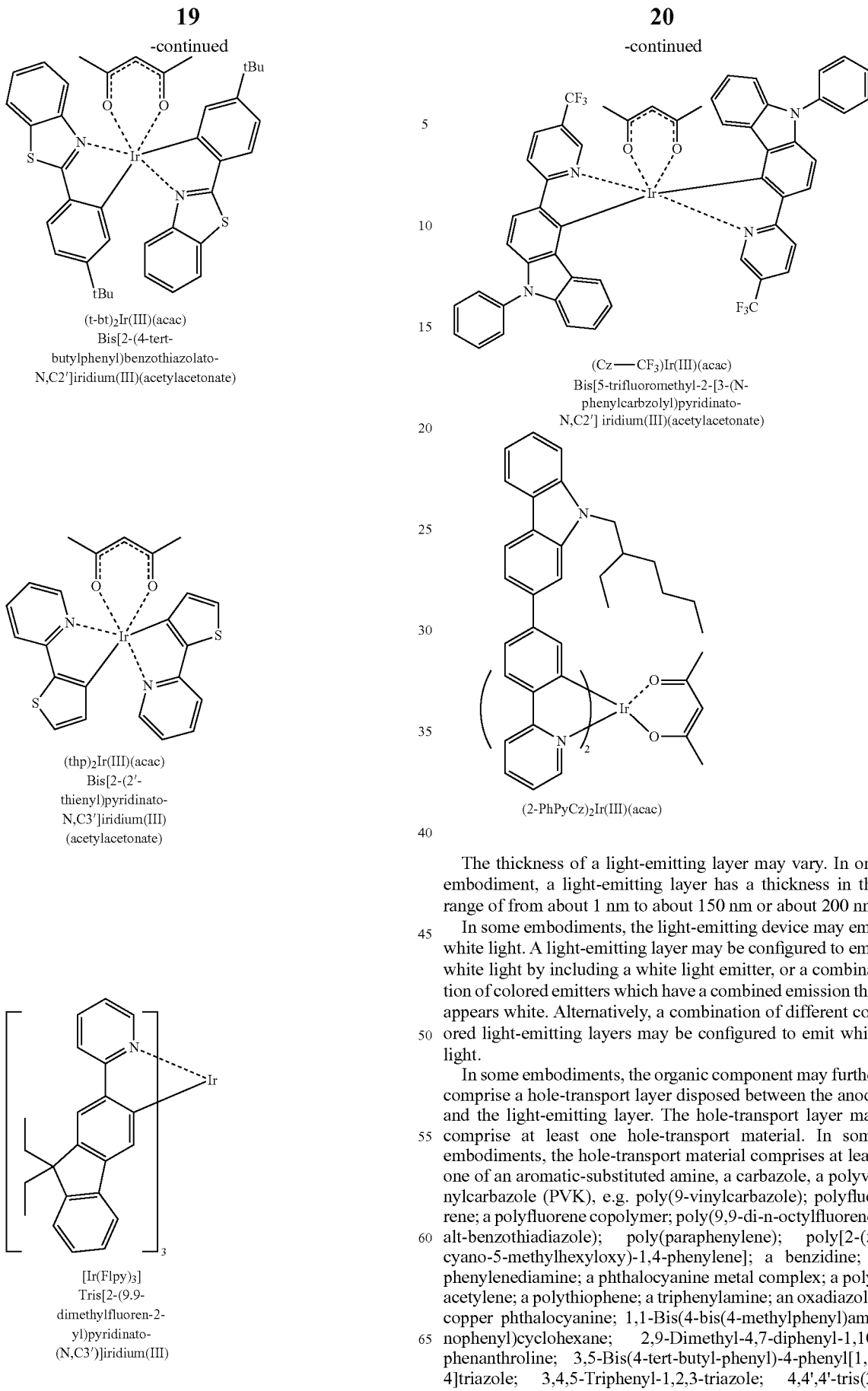

(t-bt)₂Ir(III)(acac)
Bis[2-(4-tert-butylphenyl)benzothiazolato-N,C2']iridium(III)(acetylacetonate)

(thp)₂Ir(III)(acac)
Bis[2-(2'-thienyl)pyridinato-N,C3']iridium(III)(acetylacetonate)

[Ir(Flpy)₃]
Tris[2-(9,9-dimethylfluoren-2-yl)pyridinato-(N,C3')]iridium(III)

(Cz—CF₃)Ir(III)(acac)
Bis[5-trifluoromethyl-2-[3-(N-phenylcarbzolyl)pyridinato-N,C2'] iridium(III)(acetylacetonate)

(2-PhPyCz)₂Ir(III)(acac)

The thickness of a light-emitting layer may vary. In one embodiment, a light-emitting layer has a thickness in the range of from about 1 nm to about 150 nm or about 200 nm.

In some embodiments, the light-emitting device may emit white light. A light-emitting layer may be configured to emit white light by including a white light emitter, or a combination of colored emitters which have a combined emission that appears white. Alternatively, a combination of different colored light-emitting layers may be configured to emit white light.

In some embodiments, the organic component may further comprise a hole-transport layer disposed between the anode and the light-emitting layer. The hole-transport layer may comprise at least one hole-transport material. In some embodiments, the hole-transport material comprises at least one of an aromatic-substituted amine, a carbazole, a polyvinylcarbazole (PVK), e.g. poly(9-vinylcarbazole); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; a benzidine; a phenylenediamine; a phthalocyanine metal complex; a polyacetylene; a polythiophene; a triphenylamine; an oxadiazole; copper phthalocyanine; 1,1-Bis(4-bis(4-methylphenyl)aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4'-tris(3- methylphenylphenylamino)triphenylamine (MTDATA); N,N'-bis(3-methylphenyl)N,N'-diphenyl-[1,1'-biphenyl]-4,4'-diamine (TPD); 4,4'-bis[N-(naphthyl)-N-phenyl-amino] biphenyl (α-NPD); 4,4',4''-tris(carbazol-9-yl)-triphenylamine (TCTA); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); Bis[4-(p,p'-ditolyl-amino)phenyl]diphenylsilane (DTASi); 2,2'-bis(4-carbazolylphenyl)-1,1'-biphenyl (4CzPBP); N,N'N''-1,3,5-tricarbazoloylbenzene (tCP); N,N'-bis(4-butylphenyl)-N,N'-bis(phenyl)benzidine; or the like.

In some embodiments, the organic component may further comprise an electron-transport layer disposed between the cathode and the light-emitting layer. In some embodiments, the electron-transport layer may comprise a compound represented by any of Formulas 1-13. Other electron-transport materials may be included, such as 2-(4-biphenylyl)-5-(4-tert-butylphenyl)-1,3,4-oxadiazole (PBD); 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ),2,9-dimethyl-4,7-diphenyl-phenanthroline (bathocuproine or BCP); and 1,3,5-tris[2-N-phenylbenzimidazol-z-yl]benzene (TPBI). In one embodiment, the electron transport layer is aluminum quinolate (Alq$_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

If desired, additional layers may be included in the light-emitting device. These additional layers may include an electron injection layer (EIL), a hole-blocking layer (HBL), an exciton-blocking layer (EBL), and/or a hole-injection layer (HIL). In addition to separate layers, some of these materials may be combined into a single layer.

In some embodiments, the light-emitting device can include an electron-injection layer between the cathode layer and the light-emitting layer. In some embodiments, the electron-injection layer may comprise a compound represented by any of Formulas 1-13. Other suitable electron injection materials may also be included, and are known to those skilled in the art. Examples of suitable material(s) that can be included in the electron injection layer include but are not limited to, an optionally substituted compound selected from the following: aluminum quinolate (Alq$_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl] benzene (TPBI) a triazine, a metal chelate of 8-hydroxyquinoline such as tris(8-hydroxyquinoliate) aluminum, and a metal thioxinoid compound such as bis(8-quinolinethiolato) zinc. In one embodiment, the electron injection layer is aluminum quinolate (Alq$_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof. In some embodiments, the electron-injection layer may be combined with an electron-transport layer and may comprise a compound represented by any of Formulas 1-13.

In some embodiments, the device can include a hole-blocking layer, e.g., between the cathode and the light-emitting layer. Various suitable hole-blocking materials that can be included in the hole-blocking layer are known to those skilled in the art. Suitable hole-blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4]triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton-blocking layer, e.g., between the light-emitting layer and the anode. In an embodiment, the band gap of the material(s) that comprise exciton-blocking layer is large enough to substantially prevent the diffusion of excitons. A number of suitable exciton-blocking materials that can be included in the exciton-blocking layer are known to those skilled in the art. Examples of material(s) that can compose an exciton-blocking layer include an optionally substituted compound selected from the following: aluminum quinolate (Alq$_3$), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

In some embodiments, the light-emitting device can include a hole-injection layer, e.g., between the light-emitting layer and the anode. Various suitable hole-injection materials that can be included in the hole-injection layer are known to those skilled in the art. Exemplary hole-injection material(s) include an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenylbenzidine, poly(N,N'-bis(4-butylphenyl)-N,N'-bis(phenyl) benzidine), a triphenylamine or phenylenediamine derivative such as N,N'-bis(4-methylphenyl)-N,N'-bis(phenyl)-1,4-phenylenediamine, 4,4',4''-tris(N-(naphthylen-2-yl)-N-phenylamino)triphenylamine, an oxadiazole derivative such as 1,3-bis(5-(4-diphenylamino)phenyl-1,3,4-oxadiazol-2-yl) benzene, a polyacetylene derivative such as poly(1,2-bis-benzylthio-acetylene), and a phthalocyanine metal complex derivative such as phthalocyanine copper. In some embodiments, hole-injection materials, while still being able to transport holes, may have a hole mobility substantially less than the hole mobility of conventional hole transport materials.

Light-emitting devices comprising the compounds described herein can be fabricated using techniques known in the art, as informed by the guidance provided herein. For example, a glass substrate can be coated with a high work functioning metal such as ITO which can act as an anode. After patterning the anode layer, a hole-injection and/or hole-transport layer may be deposited on the anode in that order. A light-emitting layer that includes a light-emitting component, can be deposited on the anode, the hole-transport layer, or the hole-injection layer. The light-emitting layer may contain a compound represented by any of Formulas 1-13, and/or a compound represented by any of Formulas 1-13 may be part of an electron-transport layer and/or an electron-injecting layer, deposited in that order, or may be part of an electron-injecting and electron-transport layer. The cathode layer, comprising a low work functioning metal (e.g., Mg:Ag), can then be deposited, e.g., by vapor deposition or sputtering. The device may also contain an exciton-blocking layer, an electron blocking layer, a hole blocking layer, a second light-emitting layer, or other layers that can be added to the device using suitable techniques.

In some embodiments, the OLED is made by a wet process such as a process that comprises at least one of spraying, spin coating, drop casting, inkjet printing, screen printing, etc. Some embodiments provide a composition which is a liquid suitable for deposition onto a substrate. The liquid may be a single phase, or may comprise one or more additional solid or liquid phases dispersed in it. The liquid typically comprises a light-emitting compound, a host material described herein and a solvent.

EXAMPLE 1
Example 1A
Synthesis of ET-1
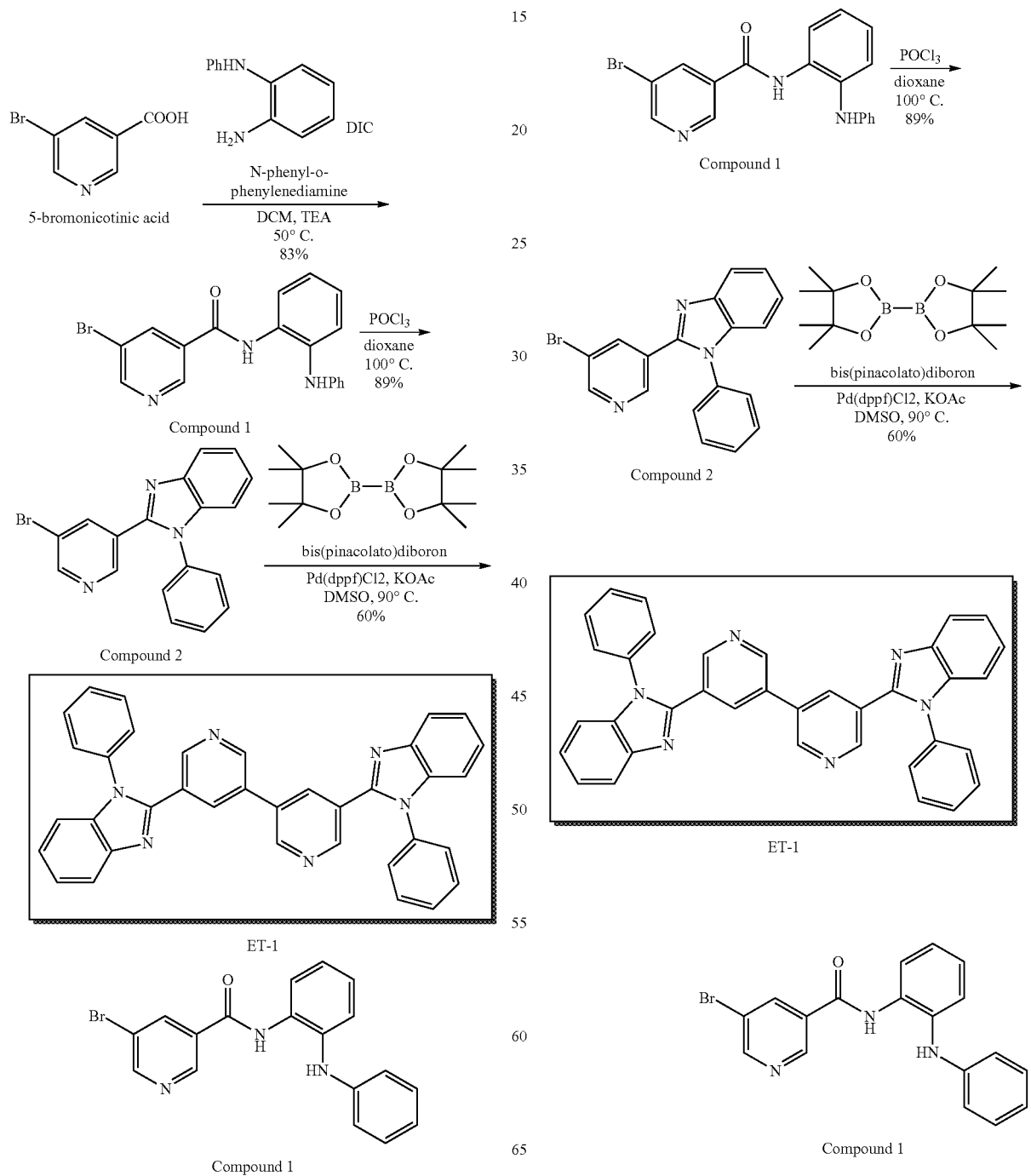

5-bromo-N-(2-(phenylamino)phenyl)nicotinamide (1): A mixture of 5-bromonicotinic acid (20.0 g, 99 mmol), N-phenyl-o-phenylenediamine (19.32 g, 105 mmol), diisopropylcarbodiimide (DIC) (26.5 g, 210 mmol), and triethylamine (TEA) (2.65 g, 27 mmol) in dichloromethane (DCM) (anhydrous, 350 mL) was heated to 50° C. and degassed with stirring overnight under argon. After cooling to room temperature (RT), the solids were filtered off. The filtrate was washed with water (2×200 mL), dried over sodium sulfate and loaded onto silica gel for purification by a flash chromatography column (gradient of 3% to 10% ethyl acetate in DCM) to yield Compound 1 (30.32 g of material; 83% yield).

Compound 2

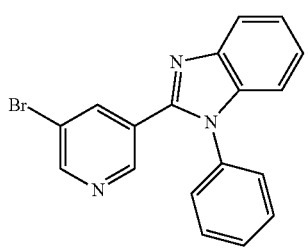

2-(5-bromopyridin-3-yl)-1-phenyl-1H-benzo[d]imidazole (2): 5-bromo-N-(2-(phenylamino)phenyl)nicotinamide (1) (20.0 g, 54.3 mmol) was dissolved in 1,4-dioxane (anhydrous, 150 mL). Phosphorous oxychloride (36 g, 235 mmol) was then added dropwise. The resulting solution was heated to 100° C. overnight with solids being formed. After cooling to RT, the mixture was poured into hexanes (250 mL) to form additional precipitate. The solids were filtered off, then redissolved in DCM (200 mL) and washed with potassium carbonate (200 mL, saturated solution). The organic phase was collected, dried over sodium sulfate, and loaded onto silica gel. Short silica plug (20% ethyl acetate in hexanes) and precipitation from hexanes yielded Compound 22 (16.86 g of 2 material; 89% yield).

ET-1

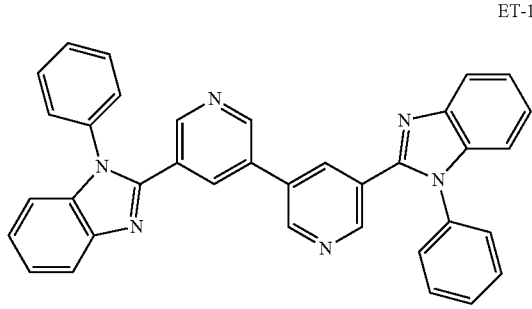 [SMILES: c1ccc(-n2c(-c3cncc(-c4cncc(-c5nc6ccccc6n5-c5ccccc5)c4)c3)nc3ccccc32)cc1]

ET-1 A mixture of 2-(5-bromopyridin-3-yl)-1-phenyl-1H-benzo[d]imidazole (2) (350 mg, 1.0 mmol), bis(pinacolato)diboron (140 mg, 0.55 mmol), potassium acetate (300 mg, 3 mmol) and bis(diphenylphosphino)ferrocene]dichloropalladium (36 mg, 0.05 mmol) in DMSO (6 mL) was heated at 90° C. overnight and degassed under argon. After cooling to RT, the whole was poured into water (50 mL), and extracted with DCM (200 mL×3). The organic phase was collected and warmed to about 40-45° C. to dissolve all suspended solid, then dried over sodium sulfate. Purification with flash chromatography column (silica gel, ethyl acetate/hexanes 4:1 to ethyl acetate to ethyl acetate/methanol 40:1) gave ET-1 as a white solid (162 mg, 60% yield).

Example 1b

Synthesis of ET-2

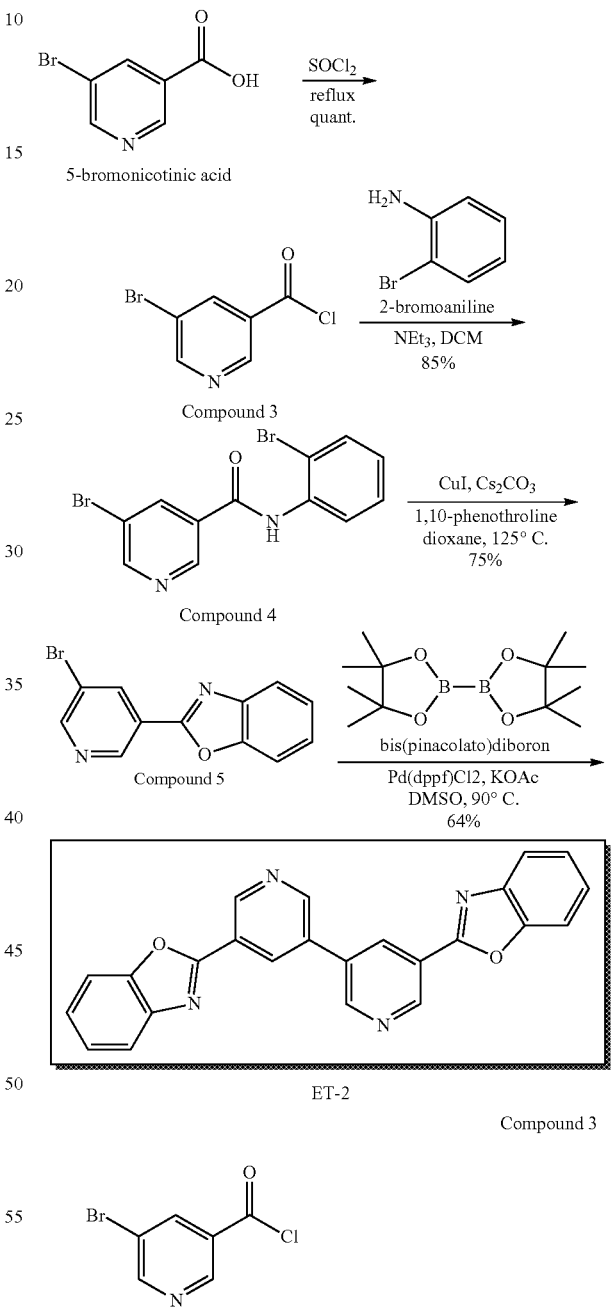

5-Bromonicotinoyl chloride (3): To a mixture of 5-bromonicotinic acid (10 g) in thionyl chloride (25 mL) was added anhydrous dimethylformamide (DMF) (0.5 mL). The whole was heated to reflux for overnight. After cooling to RT, the excess thionyl chloride was removed under reduced pressure. A white solid (3) (11 g) was obtained, which was used for the next step without further purification.

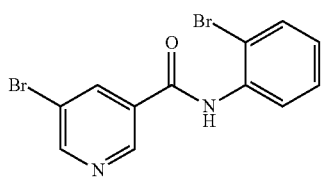

Compound 4

5-bromo-N-(2-bromophenyl)nicotinamide (4): A mixture of 5-bromonicotinoyl chloride (3) (7.5 g, 33 mmol), 2-bromoaniline (5.86 g, 33 mmol) and triethylamine (NEt₃) (14 mL, 100 mmol) in anhydrous dichlormethane (DCM) (100 mL) was stirred under argon overnight. The resulting mixture was worked up with water and extracted with dichloromethane (200 mL×2). The organic phase was collected and dried over Na₂SO₄. After concentrating to 150 mL, a white crystalline solid was crashed precipitated out. Filtration and washing with hexanes gave a white solid 4 (10.0 g, 85% yield).

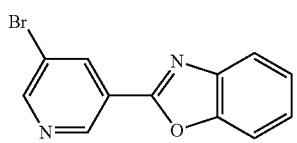

Compound 5

2-(5-bromopyridin-3-yl)benzo[d]oxazole (5): A mixture of 5-bromo-N-(2-bromophenyl)nicotinamide (4) (3.44 g, 9.7 mmol), CuI (0.106 g, 0.56 mmol), Cs₂CO₃ (3.91 g, 12 mmol) and 1,10-phenathroline (0.20 g, 1.12 mmol) in anhydrous 1,4-dioxane (50 mL) was heated at 100° C. overnight. After cooled cooling to RT, the mixture was poured into ethyl acetate (200 mL), then washed with water. The aqueous phase was extracted with ethyl acetate (200 mL×2), and the organic phase was collected and dried over Na₂SO₄, and purified by flash chromatography (silica gel, hexanes/ethyl acetate 3:1) to give a light yellow solid (5) (2.0 g, 75% yield).

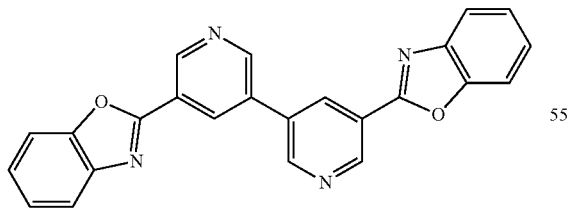

ET-2

ET-2: A mixture of 2-(5-bromopyridin-3-yl)benzo[d]oxazole (5) (550 mg, 2 mmol), potassium acetate (600 mg, 6.1 mmol), bis(pinacolato)diboron (254 mg, 1 mmol) and [1,1'-bis(diphenylphosphino)ferrocene]dichloropalladium (73 mg, 0.1 mmol) in DMSO was degassed and heated at 90° C. under argon atmosphere overnight. After cooling to RT, the whole was poured into water, filtration gave a crude solid which was washed with isopropanol and methylene chloride. A white solid ET-2 was obtained (250 mg, 64% yield).

Example 1c

Synthesis of ET-3

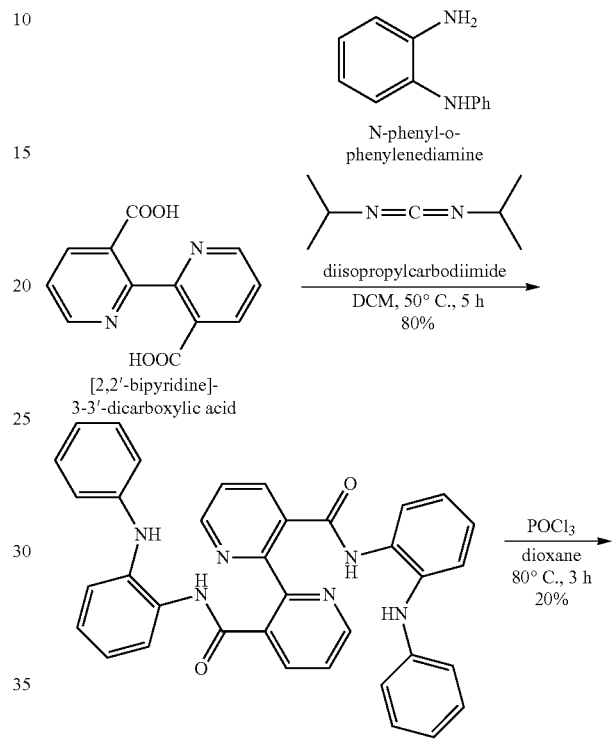

Compound 6

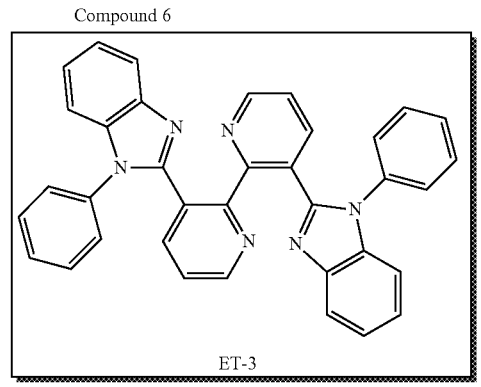

ET-3

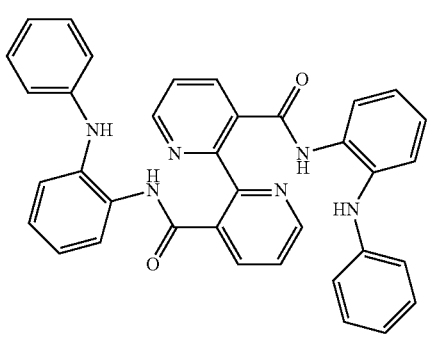

Compound 6

N3,N3'-bis(2-(phenylamino)phenyl)-[2,2'-bipyridine]-3,3'-dicarboxamide (6): To a solution of [2,2'-bipyridine]-3,3'-dicarboxylic acid (3.16 g, 13 mmol) and N-phenyl-o-phenylenediamine (5.60 g, 30 mmol) in anhydrous dichloromethane (100 mL) was added diisopropylcarbodiimide (9.68 mL, 62 mmol) dropwise, followed by triethylamine (1.2 mL, 8.6 mmol). The whole was heated at 50° C. overnight. After being cooled to RT and filtered, the filtrate was absorbed on silica gel, then purified by flash column (dichloromethane/ethyl acetate 4:1 to dichloromethane/methanol 10:1). The desired fraction was collected, concentrated, kept at −10° C. overnight. Filtratrion gave a pale yellow solid 6 (10.4 g, 80% yield).

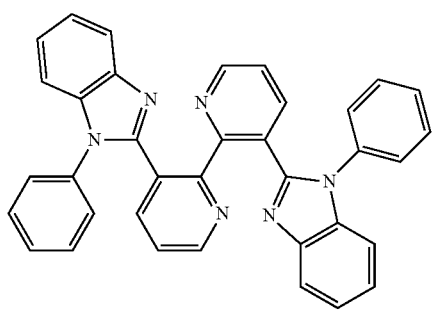

ET-3: To a solution of N3,N3'-bis(2-(phenylamino)phenyl)-[2,2'-bipyridine]-3,3'-dicarboxamide (6) (2.15 g, 3.7 mmol) in anhydrous 1,4-dioxane (50 mL) was added POCl₃ (1.72 mL). The whole was heated at 80° C. for about 3 hours. After cooling to RT, the mixture was poured into ice, then extracted with dichloromethane (150 mL×3). The organic phase was collected, washed with sodium bicarbonate solution and dried over Na₂SO₄. Then it was absorbed on silica gel, purified by flash column (dichloromethane/methanol 12:1) to give a pale yellow solid ET-3 (0.4 g, 20%).

Example 2

OLED Device Configuration and Performance

Fabrication of light-emitting device: the ITO coated glass substrates is cleaned by ultrasound in deionized (DI)-water, acetone, and in 2-propanol consecutively, then baked at 110° C. for about 3 hours, followed by treatment with oxygen plasma for about 30 min. A layer of PEDOT: PSS (Baytron P purchased from H.C. Starck) is spin-coated at about 6000 rpm onto the pre-cleaned and O₂-plasma treated (ITO)-substrate and is annealed at about 200° C. for about 30 min, yielding a thickness of around 20 nm. In a glove-box hosted vacuum deposition system at a pressure of about 1×10⁻⁷ torr (1 torr=133.322 Pa), DTASi is first deposited on top of PEDOT/PSS layer at deposition rate of about 1 Å/s, yielding a 40 nm thick film. Then, for the emissive layer (EM-1), the Host-1(2,2'-(4,4'-(9-p-tolyl-9H-carbazole-3,6-diyl)bis(4,1-phenylene))dibenzo[d]oxazole-1, 5 wt %) with yellow emitter (YE-1, 5 wt %) is codeposited at deposition rate of 1.0 and 0.05 Å/s, respectively, to form an EML layer with thickness of 8 nm. emitter is deposited at deposition rate of 1.0 and 0.05 Å/s, respectively, form an EML layer with of 8 nmYE-15.

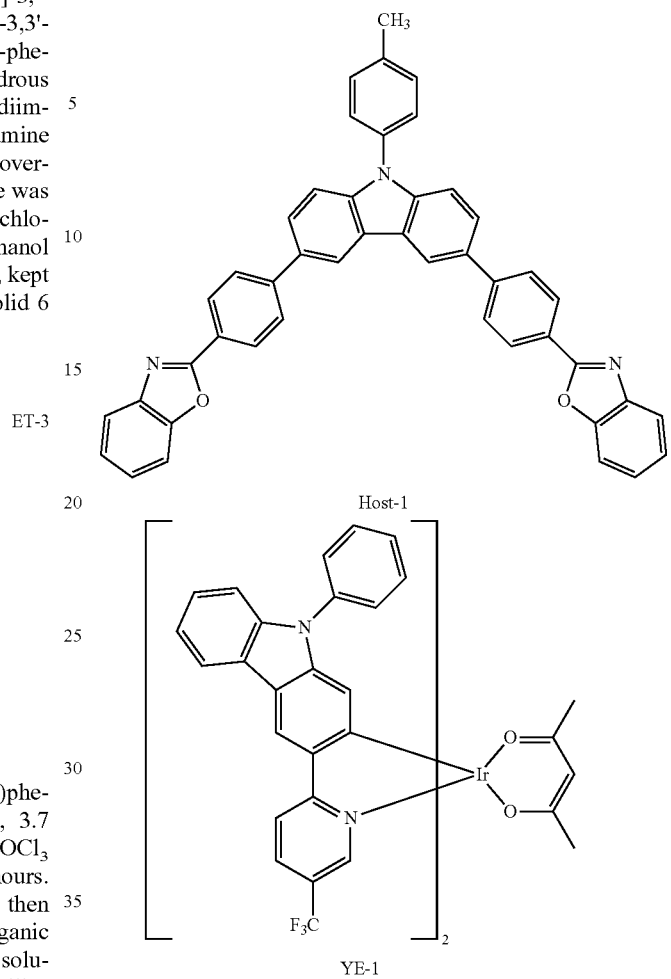

Next, the electron transport layer is deposited as ET-1 [Example 1a]) at a deposition rate around 1 Å/s to form a 40 nm thick film. LiF (0.5 nm) and Al (100 nm) is then deposited successively at deposition rates of about 0.05 and about 2 Å/s, respectively. Each individual device has a surface area of about 0.08 cm². All Electron luminescence spectra is measured on a MCPD spectrometer and I-V-L characteristics are taken with a Keithley 2400 and 2000 Meter and Si-photo diode. All device operation is performed in air after encapsulation in glove box.

A configuration of an example of a device comprising a compound described herein is shown in FIG. 1. The device comprises following layers in the order given: an ITO anode 5, a PEDOT hole-injection layer 10, a hole-transport layer 15, a light-emitting layer 25, an electron-transport layer 30, and a LiF/Al cathode 35. The electron transport layer 30 comprises a compound described herein.

At about 1000 cd/m², the driving voltage for Device A was about 4.3 volts, the power efficiency (PE) was about 51.2 lm/W at about 1000 cd/m² and about 4.3 V, and the luminance efficiency was about 70.2 cd/A. This demonstrates Device A exhibited high luminescence and power efficiency for a yellow emitting device.

Although the claims have been explained in the context of certain preferred embodiments and examples, it will be understood by those skilled in the art that the present claims extends beyond the specifically disclosed embodiments to other alternative embodiments and/or uses and obvious modifications and equivalents thereof. Thus, it is intended that the scope of the present claims should not be limited by the particular disclosed embodiments described above.

What is claimed is:

1. A compound represented by Formula 1:

Het¹-Bpy-Het² (Formula 1)

wherein Bpy is;

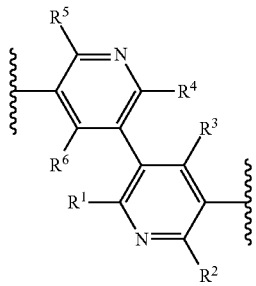

$R^1$, $R^2$, $R^3$, $R^4$, $R^5$, and $R^6$ are independently selected from the group consisting of H, $C_{1-12}$ alkyl, and optionally substituted phenyl; and Het¹ and Het² are independently substituted benzimidazol-2-yl or optionally substituted benzoxazol-2-yl.

2. The compound of claim 1, wherein $R^1$, $R^2$, $R^3$, $R^4$, $R^5$, and $R^6$ are H.

3. The compound of claim 1, wherein Het¹ is:

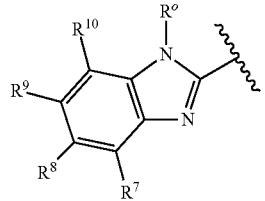

wherein $R^o$ is optionally substituted aryl;

$R^7$, $R^8$, $R^9$, and $R^{10}$ are independently selected from the group consisting of H, $C_{1-12}$ alkyl, and optionally substituted phenyl.

4. The compound of claim 3, wherein $R^7$, $R^8$, $R^9$, and $R^{10}$ are H.

5. The compound of claim 3, wherein Het¹ is:

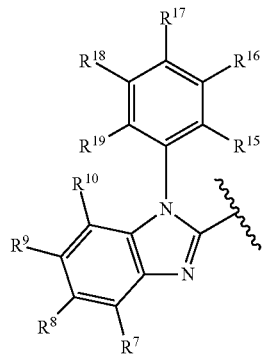

wherein $R^{15}$, $R^{16}$, $R^{17}$, $R^{18}$, and $R^{19}$ are independently selected from the group consisting of H, $C_{1-12}$ alkyl, and optionally substituted phenyl.

6. The compound of claim 5, wherein $R^7$, $R^8$, $R^9$, $R^{10}$, $R^{15}$, $R^{16}$, $R^{17}$, $R^{18}$, and $R^{19}$ are H.

7. The compound of claim 1, wherein Het¹ is:

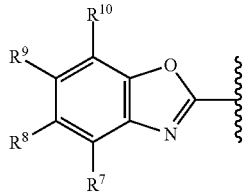

wherein $R^7$, $R^8$, $R^9$, and $R^{10}$ are independently selected from the group consisting of H, $C_{1-12}$ alkyl, and optionally substituted phenyl.

8. The compound of claim 7, wherein $R^7$, $R^8$, $R^9$, and $R^{10}$ are H.

9. The compound of claim 1, wherein Het² is:

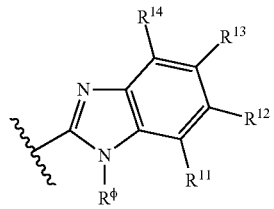

wherein $R^o$ is optionally substituted aryl;

$R^{11}$, $R^{12}$, $R^{13}$, and $R^{14}$ are independently selected from the group consisting of H, $C_{1-12}$ alkyl, and optionally substituted phenyl.

10. The compound of claim 9, wherein $R^{11}$, $R^{12}$, $R^{13}$, and $R^{14}$ are H.

11. The compound of claim 9, wherein Het² is:

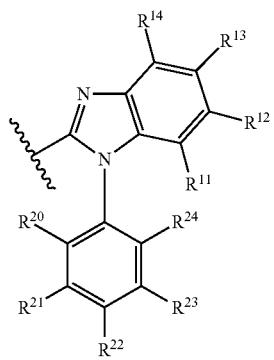

wherein $R^{20}$, $R^{21}$, $R^{22}$, $R^{23}$, and $R^{24}$ are independently selected from the group consisting of H, $C_{1-12}$ alkyl, and optionally substituted phenyl.

12. The compound of claim 11, wherein $R^{11}$, $R^{12}$, $R^{13}$, $R^{14}$, $R^{20}$, $R^{21}$, $R^{22}$, $R^{23}$, and $R^{24}$ are H.

13. The compound of claim 1, wherein $Het^2$ is:

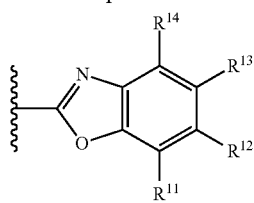

wherein $R^{11}$, $R^{12}$, $R^{13}$, and $R^{14}$ are independently selected from the group consisting of H, $C_{1-12}$ alkyl, and optionally substituted phenyl.

14. The compound of claim 13, wherein $R^{11}$, $R^{12}$, $R^{13}$, and $R^{14}$ are H.

15. The compound of claim 1, selected from the group consisting of:

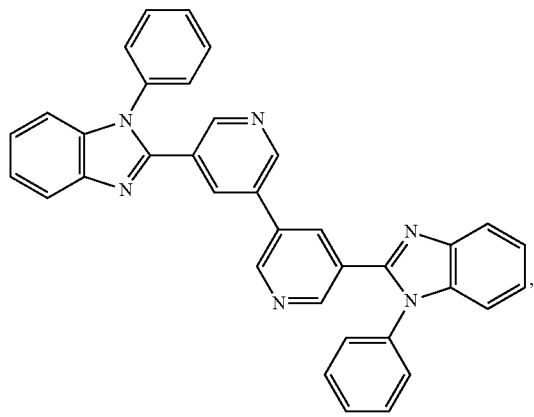

-continued
and

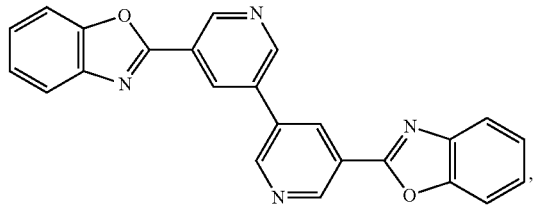

16. An organic light-emitting diode device comprising:
an organic component comprising a light-emitting component and a compound according to claim 1, wherein the compound is a host compound.

17. The organic light-emitting device of claim 16, wherein the organic component comprises an electron-injecting layer comprising the host compound, an electron- transporting layer comprising the host compound, or an electron-injecting-and transporting layer comprising the host compound.

18. A composition comprising at least 50% by weight of a compound according to claim 1.

* * * * *